US00PP13056P2

(12) United States Plant Patent
Saville

(10) Patent No.: US PP13,056 P2
(45) Date of Patent: Oct. 8, 2002

(54) MINIATURE ROSE PLANT NAMED 'SAVARALPH'

(75) Inventor: John Saville, Newburyport, MA (US)

(73) Assignee: Nor"East Miniature Roses, Inc., Rowley, MA (US)

( * ) Notice: Subject to any disclaimer, the term of this patent is extended or adjusted under 35 U.S.C. 154(b) by 45 days.

(21) Appl. No.: 09/730,317

(22) Filed: Dec. 5, 2000

(51) Int. Cl.[7] ..... A01H 5/00

(52) U.S. Cl. ..... Plt./122

(58) Field of Search ..... Plt./122, 129

*Primary Examiner*—Howard J. Locker

(57) ABSTRACT

'SAVaralph' is a new and distinct variety of miniature rose plant primarily identified by its small dark red flowers of hybrid tea form and its semi-glossy new growth flushed dark red which may appear to be glowing in the sun. Providing background for the dark red flowers and foliage on this vigorous, upright and well branched plant is the semi-glossy, dark green older foliage with good disease resistance.

1 Drawing Sheet

GENUS/SPECIES AND VARIETAL DENOMINATION OF THE PLANT

Genus/species: *Rosa chinensis 'minima'*.
Varietal Denomination: 'SAVaralph'.

BACKGROUND OF THE INVENTION

The present invention relates to a new and distinct variety of hardy, dwarf, bush type rose plant of the miniature class (*Rosa chinensis 'minima'*). The dark red buds and flowers are similar in color to 'SAVacrim' (U.S. Plant Pat. No. 9,628) and also having about the same number of petals. When fully expanded, the blooms of this new invention are near double the size of those of 'SAVacrim' even though both plants have similar habits. The buds, flowers and plant of this new invention are quite similar in form and habit to two other miniature rose plants that have the same pollen parent, 'SAVasach' (U.S. Plant Pat. No. 5,967), as does this new invention: 'SAVabear' (U.S. Plant Pat. No. 7,424) and 'SAVarain' (U.S. Plant Pat. No. 7,448).

This present variety of miniature rose was created in a greenhouse in Rowley, Mass., by crossing the following two rose plants:

The seed parent is 'SAVasach' (U.S. Plant Pat. No. 5,967).

The pollen parent is an unnamed, unintroduced seedling.

Asexual reproduction by cuttings of this new variety in Essex County, Mass. shows that all distinguishing characteristics of this rose continually come true to form.

SUMMARY OF THE INVENTION

The present invention relates to a new and distinct variety of hardy dwarf bush type rose plant of the miniature class; the variety being primarily characterized —as to novelty— by it's small dark red blooms and reddish new foliage.

The variety is further characterized by:

An abundance of those small, dark red flowers of hybrid tea form.

Semi-glossy new growth of a dark reddish green.

A slight rose fragrance.

A plant which has good vigor, is upright, well branched and compact.

A plant which grows and blooms satisfactorily both in the greenhouse and outdoors: provides decoration as a garden perennial, specimen plant or in containers and is good as a cut flower.

BRIEF DESCRIPTION OF THE DRAWING

The accompanying color photograph show specimens of the flower of this new variety in different stages of development as grown and observed in September, under plastic in Essex County, Mass.

BOTANICAL DESCRIPTION OF THE PLANT

Following is a detailed description in outline form pertaining specifically to this new and distinct variety of miniature rose plant when grown and observed in September, under plastic in Essex County, Mass. All major color plate identifications made are referring to The Royal Horticulture Society Chart except where common terms of color definition are employed.

FLOWERS

Class: Miniature rose.
Blooming habit: Continuous.
Borne: Mostly large sprays, but also singly.
Bud:
- *Size.*—Small.
- *Form.*—Ovate.
- *Color.*—When sepals first divide — a dark red, between 45A and 46A.
- *Sepals.*—Color — a medium yellow green, near 144B. characteristics — lanceolate and coarsely bearded, extending just beyond the tip of the bud, and rolling to a downward position as bloom opens and then back up to perpendicular to the stem as the hip forms.
- *Peduncle.*—Length — averaging 1 to 1½ inches. Aspect — straight. Strength — erect. Color — a dark olive green, near 146A.

Bloom:
- *Size.*—When fully expanded — 2 inches.
- *Form.*—High centered at first, becoming flat; petals remain loosely rolled outward.
- *Petalage.*—20 to 24.
- *Petaloids.*—0.
- *Fragrance.*—Slight.

*Lastingness of the bloom.*—About 6–8 days on the plant; about 5–7 days as a cut flower.

Petals:

*Texture.*—Medium.

*Appearance.*—Inside — velvety, outside — satiny.

*Form.*—Obovate, rounding up and forming a point.

*Arrangement.*—Arranged shingle-like.

*Color.*—During the first few days — a dark cherry red, near 45A and the reverse being slightly lighter, near 45C. As the bloom ages it only lightens slightly in color to near 45B on the upper surface and between 53B and 53C on the reverse.

*General tonality.*—Dark red.

REPRODUCTIVE ORGANS

Stamens, filaments and anthers:

*Arrangement.*—Regularly arranged around styles.

*Quantity.*—Ordinary.

*Filaments.*—Length — varying from 3/32 to 3/16 inch. General color — at their base, a very pale yellow (near 11D) and toward the tip, a very pale, light red.

*Anthers.*—Color — dark yellow, near 21B.

Pollen:

*Color.*—A slightly darker yellow than the anthers, near 21A.

*Quantity.*—Ample.

Pistils, styles and stigmas:

*Quantity.*—Many for the small size of the receptacle.

*Styles.*—Thin, uneven length, Color — medium red.

*Stigmas.*—Color — near white.

Hips:

*Shape.*—Near globular.

*Size.*—Up to 7/8 inch.

*Color.*—Deep orange, from near 25A and becoming near 169B and near 46A when in full sun.

PLANT

Habit: Upright and compact.

Growth: Vigorous and uniformly branched, maturing at a height near 18 inches.

Length of flowering stem: Up to 5 inches.

Foliage:

*Size.*—Medium.

*Quantity.*—Abundant.

*Color.*—New foliage — both upper surface and underside are flushed to a dark burgundy, near 187B. Older foliage — dark green, near 147A, on the upper surface and a medium green, near 147B, on the reverse.

*Texture.*—Semi-glossy on the upper surface and matte on the underside.

*Leaflets.*—Usually 3 to 5 leaflets, but occasionally may have 7. Shape — oval, pointed. Edge — very fine serration.

*Leaf stem.*—Olive green, near 146A, and the underside of the leaf stem being only slightly lighter green and matching the undersides of the older foliage, near 147B.

*Stipules.*—Slightly bearded, short — averaging 1/4 inch in length.

Disease resistance: good resistance to black spot and downy mildew, no rust observed.

Wood: Smooth with new wood being yellow green and heavily flushed with the dark burgundy, near 187B, and old wood a dark green, near 137A.

Thorns:

*Quantity.*—On main stalks — very few and on laterals few.

*Form.*—A flat base tapering to a fine point, straight and being of medium length.

*Color when young.*—A very light burgundy red.

Winter hardiness: Needs protection in cold climates.

I claim:

1. A new and distinct variety of hardy miniature rose plant substantially as illustrated and described, primarily characterized by small dark red buds and flowers of hybrid tea form on an upright and compact plant with semi-glossy and reddish new growth.

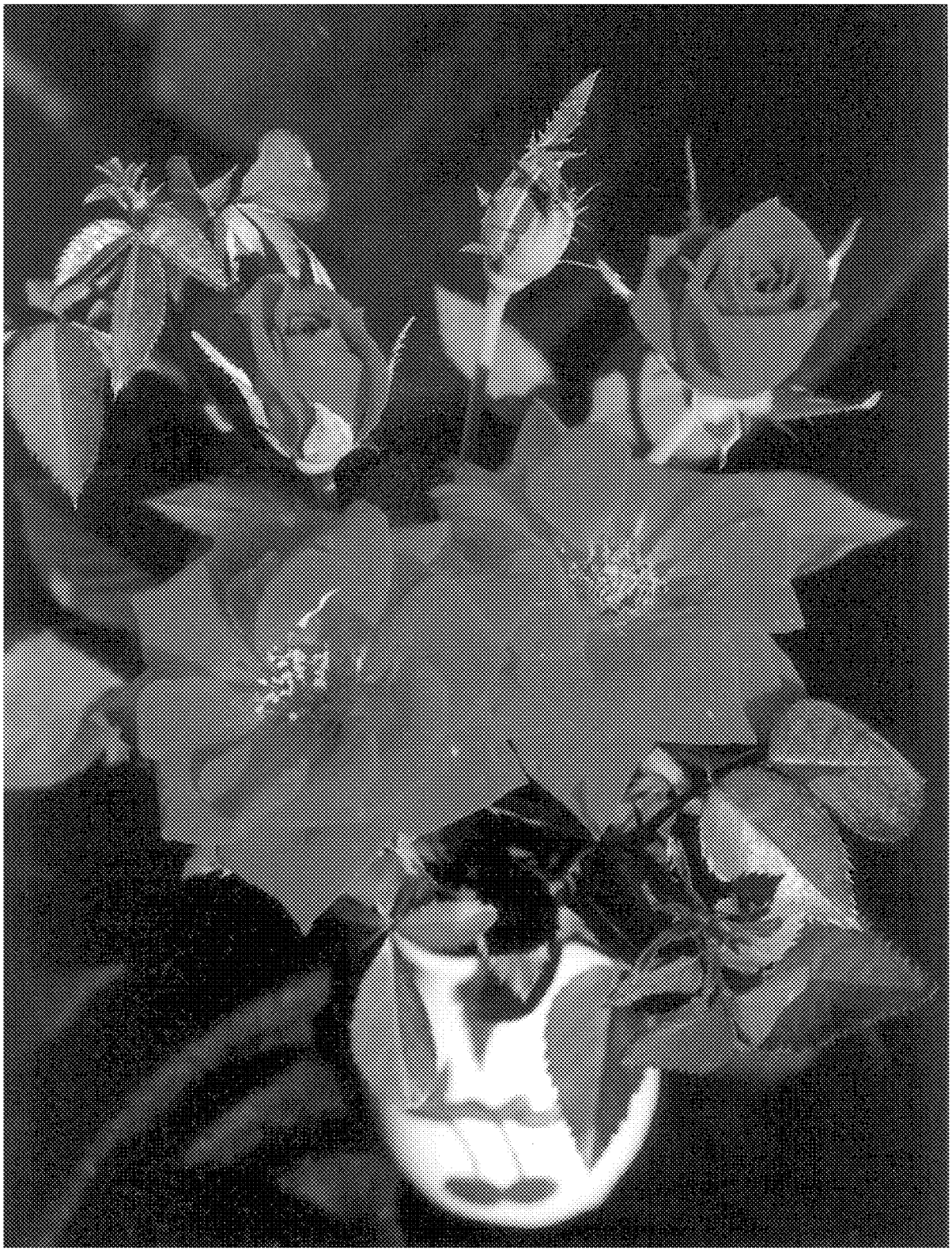

* * * * *